United States Patent
Abell

[19]

[11] Patent Number: 6,138,984
[45] Date of Patent: Oct. 31, 2000

[54] UNITARY SPHINCTER VALVE ASSEMBLY

[75] Inventor: Roy Abell, Duluth, Ga.

[73] Assignee: Innovatek Medical Corporation, Norcross, Ga.

[21] Appl. No.: 08/811,816

[22] Filed: Mar. 4, 1997

[51] Int. Cl.⁷ ................................................. F16K 7/07
[52] U.S. Cl. ...................................... 251/5; 251/4
[58] Field of Search ............................. 251/4, 5

[56] References Cited

U.S. PATENT DOCUMENTS

| | | | |
|---|---|---|---|
| 2,590,215 | 3/1952 | Sausa | 251/5 X |
| 3,441,245 | 4/1969 | Holland | 251/5 |
| 3,490,732 | 1/1970 | Leroy | 251/5 |

Primary Examiner—John Fox
Attorney, Agent, or Firm—Womble Carlyle Sandridge & Rice

[57] ABSTRACT

A sphincter valve for controlling the flow of fluid through a fluid delivery line has a body molded of a unitary piece of substantially flexible silicone material. The body is formed with an outer shell, and interior tube disposed within said outer shell, an end portion, and a pressure chamber defined between the outer shell and the interior tube. A separate end cap is secured to and closes the end of the body opposite the end portion thereof and a central passageway extends through the interior tube and through the ends of the valve. In use, the valve is spliced in a fluid delivery line and the pressure chamber is coupled to a source of selectively deliverable pressurized air. When pressurized air is forced into the pressure chamber, the inward force created by the pressure collapses the interior tube onto itself shutting off flow through the valve.

15 Claims, 3 Drawing Sheets

UNITARY SPHINCTER VALVE ASSEMBLY

TECHNICAL FIELD

This invention relates generally to valves and more specifically to pneumatically or hydraulically controllable sphincter valves.

BACKGROUND OF THE INVENTION

In a variety of medical applications, valves are used to control the inflow and outflow of fluids into and out of a patient's body. Such applications include, among others, blood transfusions, stomach evacuations, heart lung machine procedures, and colonic lavage for the removal of fecal impactions from a patient's bowels. In the case of colonic lavage, it is common that a first valve is connected in the liquid supply line of the lavage apparatus to control the inflow of water or other lavage liquid into a patient's colon for hydrating and loostening impacted fecal material. A second valve is connected in the drain line. This second valve usually is closed during fluid inflow to allow the bowels of the patient to fill with fluid. The second valve can then be opened to allow fluid and loosened fecal material to flow out of the patients colon to an appropriate receptacle.

Valves used in colonic lavage systems and, indeed, in other medical applications, are subject to a number of relatively severe operational constraints. First, such valves must be extremely reliable because the lives of patients can and often are dependent upon their flawless operation. In addition, the valves must be gentle in that they must open and close in such a way that fluid flow is not stopped or started abruptly, which can shock a patient's system or damage delicate tissues. This is particularly true in the case of colonic lavage procedures because colon walls are thin and subject to rupture under abrupt stresses. It is also important in colonic lavage procedures that valves used in the system have the ability to cause a rapid pulsing of the lavage inflow liquid to aid in the loosening of fecal impactions. In addition, such valves must be opened reliably and automatically in response to excess back pressure from the colon in order to prevent damage to the colon as a result of excess fluid pressure.

In the past, a variety of valves have been used in medical procedures such as those discussed above. In many cases, a sphincter valve design has been adopted because of its many advantages. In a sphincter valve, communication through the valve is closed by squeezing or collapsing a flexible tube within the valve through which the fluid passes. The valve is opened by releasing the flexible tube to allow the fluid to flow. This squeezing and releasing has been accomplished in a number of ways. In a heart lung machine, for example, the tube is squeezed and released by moving rollers that intermittently engage, compress, and roll along a short length of the tube. This action not only closes the valve, it also has the effect of pumping fluid intermittently through the tubing. In another type of sphincter valve, a mechanical plunger is actuated to engage and compress the flexible tube to close off communication therethrough.

One sphincter valve design that has proved itself reliable is the pneumatically controlled sphincter valve. Such valves have proven particularly useful in colonic lavage systems. In these types of valves, a short, flexible, collapsible tube is enclosed within a pressure chamber coupled to a source of compressed air. The tube is coupled or spliced into the lavage liquid delivery line to control lavage fluid inflow. A similar valve may be spliced into the waste drain line to control the flow of contaminated fluid from the patient's colon. When it is desired to close one of the valves, pressurized air is injected into the pressure chamber. This generates inward force that collapses the interior tube and shuts off the flow therethrough.

In the past, pneumatic sphincter valves have been constructed of a hard injection molded plastic outer shell having corresponding injection molded end caps that can be glued in place to form a generally cylindrical pressure chamber. A short tubular nipple communicates with the interior of the chamber and projects outwardly from the side thereof for selective delivery of pressurized air to the pressure chamber. Each of the end caps is molded with a short tubular coupler that extends and communicates through the end cap and that has an interior end within the chamber and an exterior end outside the chamber. A length of flexible surgical tubing is secured at its ends to the interior ends of the couplers communicating therebetween. The entire assembly is spliced into a liquid delivery or drain line by cutting the line if necessary and coupling the cut ends of the line to the exterior portions of the tubular couplers. Thus, fluid can flow from one section of the line, through the flexible tube within the chamber, and into the other section of the line. The tubular nipple is coupled to a source of selectively deliverable compressed air. When it is desired to shut the valve off, compressed air is injected into the pressure chamber, exerting pressure on the flexible tube within to compress and collapse the tube, thus shutting off the flow. For opening the valve, the pressure is simply released.

While the just described pneumatic sphincter valve design has proved useful and reliable, it nevertheless embodies certain problems and shortcomings inherent in its design. For example, the valve is relatively expensive to manufacture because key components are injection molded. Further, the valve is time consuming and thus expensive to fabricate because the internal flexible tube must be installed manually and the end caps and other components must be glued to the chamber by hand. The hard plastic shell of the chamber can shatter if dropped and is uncomfortable to the skin of a patient such that the valve cannot comfortably be laid or rested on the patient during use. Finally, since the flexible internal tube of the valve is separate and made of a different material than other valve components, it can, under certain circumstances, come loose from the couplers within the valve causing the valve to fail and risking contamination of the compressed air supply.

For these reasons, and particularly due to the expense of production and fabrication, conventional pneumatic sphincter valves have not been economical for use with disposable colonic lavage kits designed to be discarded after a single use. Accordingly, such disposable kits have been expensive and thus not easily available to lower income persons or patients on fixed incomes. There is thus a need for a reliable, unbreakable, and economical sphincter valve that can be used with colonic lavage and other medical procedures and discarded after use. It is to the provision of such a sphincter valve that the present invention is primarily directed.

SUMMARY OF THE INVENTION

Briefly described, the present invention, in one preferred embodiment thereof, comprises a unitary sphincter valve assembly intended primarily for use in medical applications such as colonic lavage procedures. The assembly preferably is molded in a single molding step from a translucent, opaque, or pigmented pliant silicone material. The completed assembly is formed from two parts, a main body and an end cap, each of which is molded of a unitary piece. The main body of the assembly is formed to define a generally cylindrical relatively thick walled outer shell and a relatively thin walled interior tube that extends coaxially within the outer shell and that has a central passageway. A pressure chamber is defined between the outer shell and the interior tube and the central passageway continues and communicates through the end of the main body where a female coupling nipple provides a means for coupling the valve in a fluid delivery line. The outer shell of the main body is formed with a tubular coupling nipple that projects outwardly from the wall of the outer shell and communicates with the pressure chamber between the outer shell and the interior tube.

Molded simultaneously with and of the same silicone material as the main body is an end cap that, in use, is inserted in the other end of the main body to form the completed valve assembly. The end cap has a central passageway, an inwardly projecting plug, a shoulder or flange, and an outwardly projecting female coupling nipple similar to the coupling nipple formed on the opposite end of the valve. When installed in the end of the main body, the plug is sealingly received within the end of the interior tube so that the tube passageway is continued through the end cap and through the coupling nipple to define a continuous passageway through the valve. The shoulder or flange of the valve abuts and is sealed about the end of the outer shell of the main body to close off the pressure chamber defined between the outer shell and the interior tube.

In use, the valve assembly of this invention functions in much the same way as prior art sphincter valves. Specifically, the valve is spliced in a fluid flow line by coupling one section of the line to the coupling nipple on one end of the valve and coupling the other section of the line to the coupling nipple on the opposite end of the valve. Thus, fluid is free to flow through the central passageway of the valve. An air pressure supply tube is coupled to the coupling nipple projecting from the main body for selective delivery of pressurized air to the pressure chamber.

With no pressurized air supplied to the pressure chamber, fluid is free to flow through the valve unimpeded. In this condition, the valve is open. When it is desired to close the valve, pressurized air is supplied to the pressure chamber. As the air enters the chamber, it exerts inward force on the interior tube causing it to collapse on itself closing off communication through the valve and shutting off the flow of fluid. Thus, the valve can be opened and closed by selectively supplying pressurized air to and releasing the pressure from the pressure chamber of the valve. In practice, the valve can be cycled in this way up to several times per second if desired.

It has been found that the valve of this invention, in addition simply to opening and closing, provides an added function that is particularly benificial in colonic lavage applications. Specifically, as pressurized air is supplied to the pressure chamber, the interior tube first collapses at its center and continues to collapse toward the ends of the valve as it closes. This acts to squeeze the fluid within the passageway out of the valve causing a short pulse of fluid through the fluid flow line. When the valve is cycled rapidly, the result is a pulsating flow of fluid, which, when the valve is used in the fluid supply line of a colonic lavage apparatus, acts to loosen and dislodge impacted fecal material in a patient's colon. While this pulsing function also occurs with prior art hard shell sphincter valves, it has been found that the flexibility of the unitary silicone structure of the present invention provides pulsing action superior to that of prior art valves.

Thus, it is an object of this invention to provide a sphincter valve that is inexpensive to manufacture relative to prior art valves but that functions as well or better.

Another object of the invention is to provided a sphincter valve that is reliable yet economical enough to be discardable after a single use.

A further object of the invention is to provide a sphincter valve that can be assembled quickly and with minimum labor.

A still further object of the invention is to provide a sphincter valve having a soft body that is not uncomfortable to the skin of a patient so that it can be laid or rested on a patient's body during use if desired.

These and other objects, features, and advantages of the present invention will become apparent upon review of the detailed description set forth below when taken in conjunction with the accompanying drawings, which are briefly described as follows.

BRIEF DESCRIPTION OF THE DRAWINGS

FIG. 4 illustrates an alternate embodiment of the end plug of the unitary sphincter valve assembly.

DETAILED DESCRIPTION OF THE PREFERRED EMBODIMENT

Figure 1:
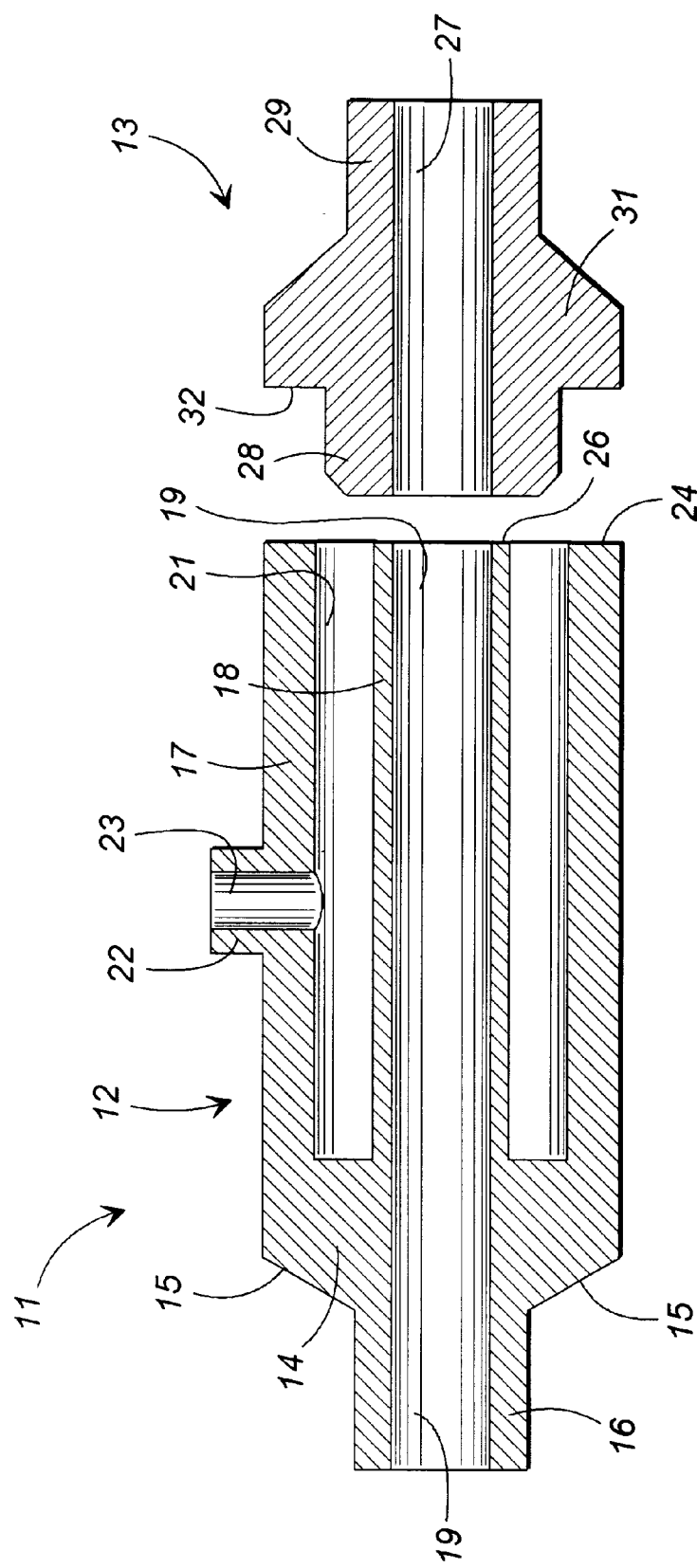
FIG. 1 is a side cross-sectional view of a unitary sphincter valve assembly that embodies principles of the present invention in a preferred form.

Referring now to the drawings, wherein like numerals refer to like parts throughout the several views, FIG. 1 illustrates in cross-section a sphincter valve assembly that embodies principles of the present invention in a preferred form. The assembly 11 comprises two components, a main body 12 and an end cap 13. Both the main body 12 and the end cap 13 preferably are molded at the same time and in a common mold. Further, both components in the preferred embodiment are formed of a flexible somewhat rubber like material such as, for example, a silicone, a silicone rubber compound, or another synthetic rubber material. Latex materials can also be used, but they are not preferred for applications where the valve is likely to come into contact with a patient's skin because many patients have latex allergies. In any event, the material can be uncolored or pigmented if desired and preferably is translucent or partially transparent so that a user can observe the operation of and fluid flow through the valve.

The main body 12 is formed to define a generally cylindrical outer shell 17 that surrounds and is coaxially aligned with a smaller interior tube 18. The outer shell 17 is molded to have relatively thick walls so that it is substantially rigid, although some flexibility is provided in the outer shell because of the flexible nature of the silicone material from which it is molded. Conversely, the walls of the interior tube are relatively thin compared to those of the outer shell so that the interior tube is flexible and can be collapsed upon itself under the influence of appropriate inward force applied to the outside of the tube. The interior tube 18 is spaced from the inner walls of the outer shell 17 so that an annular or cylindrical pressure chamber 21 is defined between the outer shell and the interior tube.

The main body 12 is also formed with an end portion 14 that is integrally molded with the outer shell and the interior tube and from which they extend. The end portion 14 is molded with a shoulder 15 from which a female coupling nipple 16 axially extends. The end portion closes off the pressure chamber at the end of the valve and supports the end of the interior tube 18 relative to the outer shell 17. The central passageway 19 of the interior tube 18 extends continuously through the end portion 14 of the main body and axially through the coupling nipple 16 to define a continuous uninterrupted passage through the valve. At the other end of the main body 12, the outer shell 17 terminates in an end 24 and the interior tube 18 terminates in an end 26. In the preferred embodiment, the ends 24 and 26 and substantially coplaner; however, this is not a requirement and one of the ends could well be recessed with respect to the other end.

The end cap 13 is formed with a central axially extending passageway 27 that preferably has the same diameter as the central passageway 19 defined through the main body 12. The end cap 13 is also formed with a radially extending flange 31, an inwardly extending plug 28, and an outwardly extending coupling nipple 29. The flange 31 defines a shoulder 32 that is sized and configured to abut the end 24 of the outer shell 17 when the end cap 13 is installed in the end of the main body as described in more detail below.

The outside diameter of the inwardly extending plug 28 is larger than the inside diameter of the central passageway 19 of the interior tube and preferably is substantially the same as the inner diameter of the pressure chamber 21. With this configuration, the end 26 of the interior tube 18 and the end 24 of the pressure chamber can be stretched to a larger diameter with an appropriate stretching tool and the inwardly extending plug 28 can be inserted into the stretched ends as the end cap is installed. When the stretched ends are released, they tend to return to their original size thereby closing and sealing around the outside of the plug 28. More specifically, the end 24 of the pressure chamber, when released, closes around the plug 28 and around the tube 18 capturing the end 26 of the tube between the plug and the interior wall of the pressure chamber. This securely fixes the end of the tube and forms a continuous sealed passageway completely through the valve from the left coupling nipple 16, through the interior tube 18, and out the right coupling nipple 29. It is also preferable when installing the end cap that a bead of silicone adhesive be applied between the end 24 of the outer shell 17 and the shoulder 32 of the end cap. In this way, the pressure chamber 21 is reliably sealed against any leakage between the end of the main body 12 and the end cap 13.

A female coupling nipple 22 projects radially outwardly from the outer shell 17 and has a central passageway 23 that communicates with the pressure chamber 21. As described below, the nipple 22 is adapted to be coupled to a pressurized air hose for the selective delivery of pressurized air to the pressure chamber 21.

Figure 2:
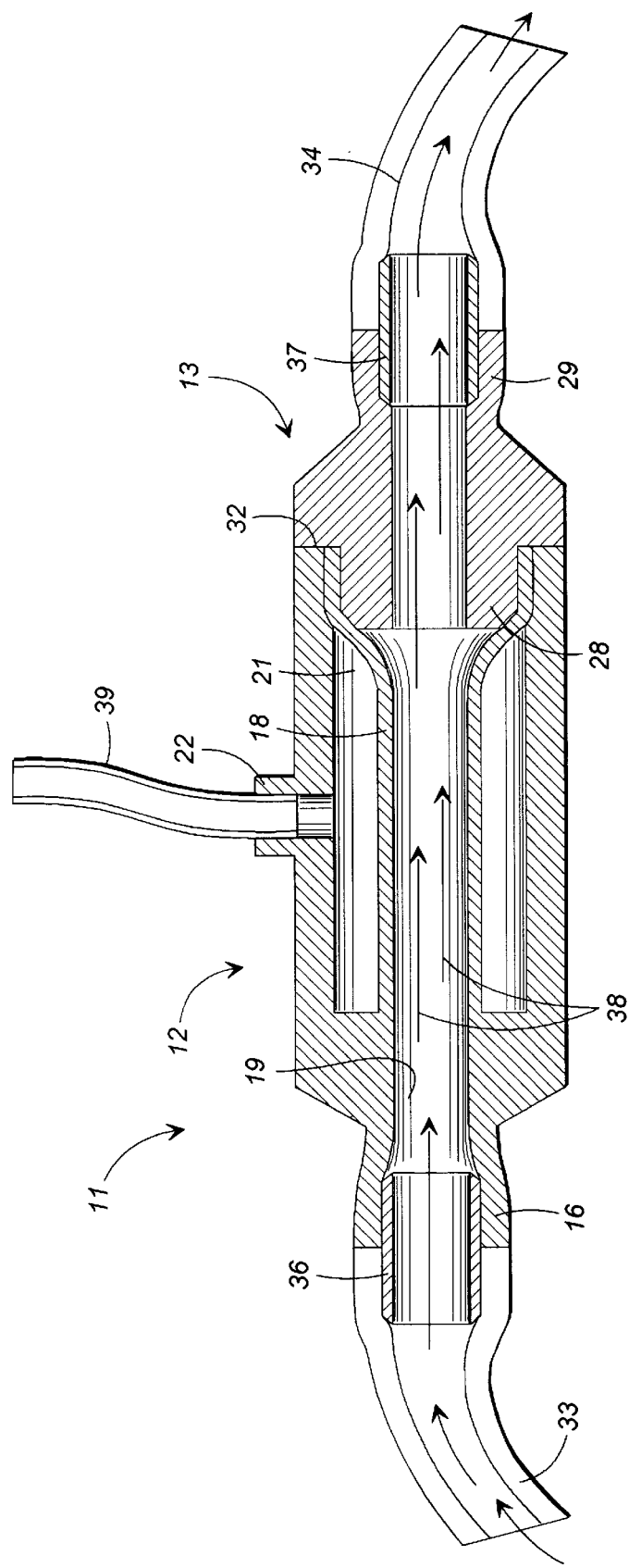
FIG. 2 is a cross-sectional view of the valve of this invention shown assembled, spliced in a fluid flow line, and in its open condition.

FIG. 2 illustrates the sphincter valve of this invention fully assembled and spliced into a fluid delivery line for controlling the flow of fluid therethrough. In FIG. 2, the valve is shown in its open condition allowing fluid to flow through the valve and through the fluid delivery line. The end cap 13 is seen inserted in the end of the main body 12 with the end of the interior tube 28 and the end of the pressure chamber stretched and sealed about the inwardly projecting plug 28. The shoulder is sealed against the end of the outer shell with an appropriate silicone adhesive to seal off the end of the pressure chamber 21.

One end 33 of the fluid delivery line is coupled to the coupling nipple 16 at the left end of the valve by means of a cylindrical adapter 36. Specifically, the adapter 34 fits tightly within both the end of the coupling nipple and the end of the delivery tube to couple the two together. Other coupling means can also be used. For example, the coupling nipple might simple be stretched, the end of the fluid delivery tube inserted, and the nipple released to constrict and seal about the end of the tube. These and other means of coupling the delivery tube to the valve are contemplated and are within the scope of the present invention.

Similarly, the other end 34 of the fluid delivery line is coupled via adapter 37 to the coupling nipple 29 at the other end of the valve. Again, while an adapter is used, other coupling means might be employed. Thus it is seen that the flow of fluid is free to continue from the left portion of the fluid delivery line, through the interior tube of the valve, and into the right portion of the fluid delivery line as if the valve were not in the system. A pressurized air supply line 39 is coupled to the coupling nipple 22 and communicates with the pressure chamber 21 within the valve. Through the supply line 39, pressurized air can be selectively injected into the pressure chamber for closing the valve as described in more detail below. In FIG. 2, no pressure has been applied to the pressure chamber and the valve is fully open allowing the free flow of fluid as indicated by arrows 38.

It will be appreciated from FIG. 2 that the flexible nature of the silicone material from which the valve is molded contributes to its functionality, allowing quick and easy coupling of the valve to the various tubes of the fluid delivery and pneumatic control systems. This represents and advantage over prior art sphincter valves with hard plastic shells, wherein the various tubes and supply lines must generally be coupled to the valve with ancillary clamps or other appropriate fastners.

Figure 3:
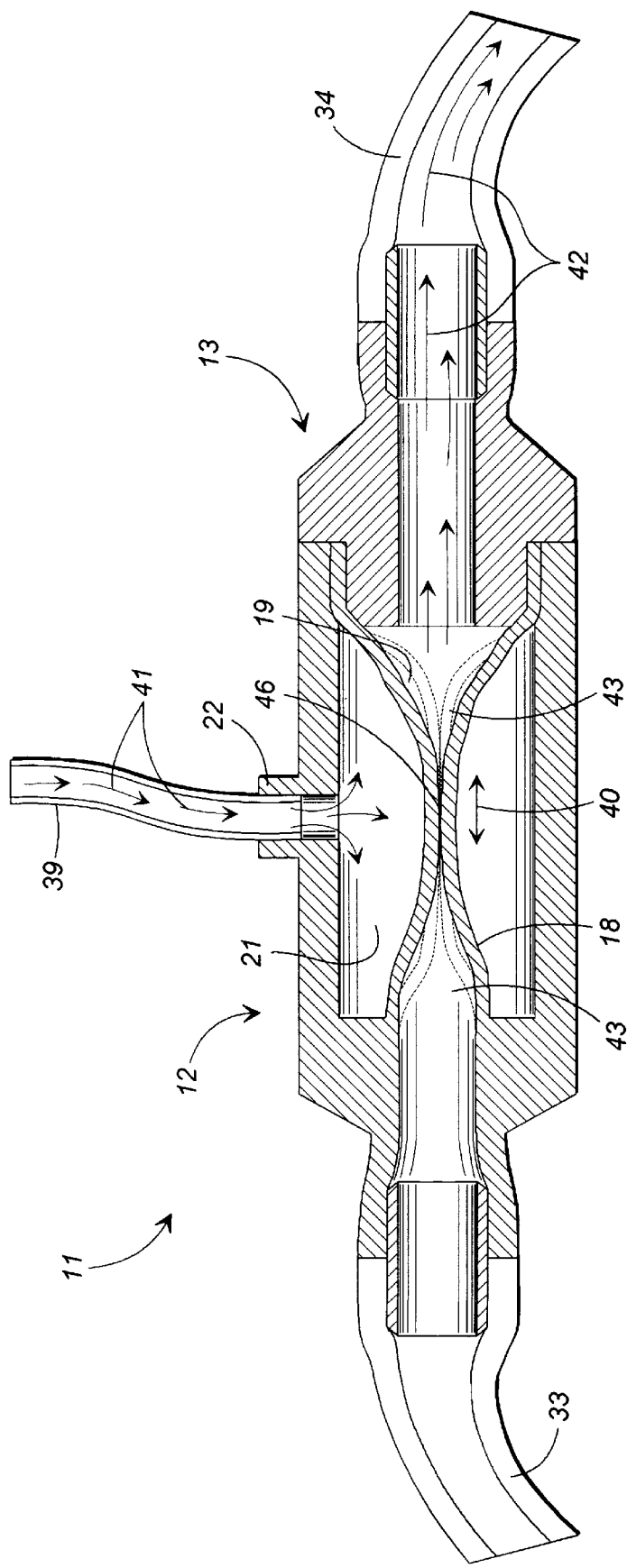
FIG. 3 is a cross-sectional view of the valve of this invention shown assembled, spliced in a fluid flow line, and in its closed condition.

FIG. 3 illustrates operation of the sphincter valve of this invention to close off a flow of fluid and to provide a momentary pulse of fluid through the fluid delivery line. As in FIG. 2, the valve 11 is seen to be spliced into a fluid delivery line at the opposed ends of the valve. The pressurized air supply line 39 is coupled to the main body 12 at the coupling nipple 22 and is in communication with the pressure chamber 21 for delivery of pressurized air thereto. In FIG. 3, pressurized air, or other appropriate gas as desired, is shown at 41 being forced into the pressure chamber 21 through the pressurized air supply line 39. The pressurized air can originate from any appropriate source connected to the other end of the supply line 39 (not shown), such as, for example, a pump or pressurized air tank and associated control system, a hand operated pump, or other source. The actual means of delivering pressurized air to the pressure chamber can vary widely depending upon the particular application to which the valve is put.

As pressurized air is delivered to the pressure chamber 21, the pressure within the chamber gradually increases as a function of the rate of pressurized air flow. This, in turn, exerts increasing inward force on the interior tube 18 and corresponding outward force on the interior walls of the outer shell 17. Since the walls of the interior tube are substantially thinner than the walls of the main body, the increasing force causes the interior tube to begin to collapse upon itself. Eventually, the force becomes sufficient to cause the walls of the interior tube 18 to meet and contact each other intermediate the ends of the tube as illustrated at 46 in FIG. 3. At this point, the flow of fluid through the fluid delivery line is shut off and the valve is in its closed condition.

If desired, pressurized air can continue to be forced into the pressure chamber 21 after the initial closing of the valve. This further increases the pressure within the pressure chamber 21 causing the interior tube 18 to collapse further upon itself from its mid-portion toward its opposed ends, as illustrated in phantom lines at 43 in FIG. 3. This action, in turn, squeezes out fluid within the interior tube causing a surge or pulse of fluid through the fluid delivery line as indicated at 42 in FIG. 3. It has been found that the flexible unitary nature of the entire valve assembly, including the walls of the main body, improves the efficiency of this process as the main body walls bulge slightly outwardly in response to the increasing pressure.

The pulse action of the sphincter valve of this invention provides significant advantages in many applications, and particularly in colonic lavage procedures. In such procedures, the valve can be opened and closed rapidly up to several times per second if desired. This causes a distinctly pulsed flow of fluid into a patient's colon as a result of the surge or pulsed action provided by the opening and closing valve. Such a pulsed flow has been found to be very beneficial in colonic lavage procedures for dislodging and hydrating impacted fecal material in a patient's colon so that the material can be removed from the colon through an associated drain line. Thus, the unique sphincter valve of the present invention provides benefits and advantages and does so at a cost and with a complexity far less than prior art sphincter valves. Thus, the valve can simply be discarded after use, making it ideal for disposable fluid delivery kits for use in medical procedures. Disposability is important in many medical procedures and particularly procedures such as colonic lavage performed at home because the valves become contaminated after use and cannot easily be cleaned. Further, the valve of this invention is relatively soft and is not uncomfortable to the skin of a patient. It can thus be rested on a patient's skin during a procedure if necessary without being uncomfortable.

The invention has been described herein in terms of preferred embodiments and methodologies. It will be apparent to those of skill in the art, however, that various modifications might well be made to the illustrated embodiments within the scope of the invention. For example, while silicone or a silicone compound has been illustrated as the preferred material from which the valve is molded, other appropriate materials might well be substituted. Further, the size and relative dimensions of the various components of the valve might be different from those illustrated in the drawings depending upon the particular purpose for which it is intended. For example, the valve could be made long and thin in order to increase the relative length of the interior tube and provide a more pronounced pulsed action as the valve is closed. Finally, the sphincter valve of this invention has been illustrated and described as a pneumatically controlled device wherein air or gas is used to open and closed the valve. In certain applications, however, it might be desirable to employ a fluid to open and close the valve rather than air. In such cases, the valve would be hydraulically controlled rather than pneumatically controlled, but the principles of operation would remain substantially the same. Finally, the invention has been described in terms of a single unitarily molded valve. The same principles could be applied to a unitarily molded gang valve wherein two or more individually controllable valves are molded within a single unitary body. These and other additions, deletions, and modifications might well be made to the disclosed embodiments by those of skill in the art without departing from the spirit and scope of the invention as set forth in the claims.

What is claimed is:

1. A sphincter valve assembly for use in controlling the flow of fluid through a fluid delivery line, said sphincter valve assembly comprising:

a main body unitarily molded from a substantially flexible material;

said unitarily molded main body being formed to define a first end portion, an outer shell extending from said first end portion to a free end and having a wall of a first predetermined thickness, and an interior tube extending from said first end portion to a free end and having a wall of a second predetermined thickness less than said first predetermined thickness;

said interior tube being disposed within said outer shell to define a pressure chamber between said interior tube and said outer shell;

said main body further forming a first coupling nipple communicating with said pressure chamber for coupling said pressure chamber to a source of selectively deliverable pressurized fluid;

a central passageway extending through said first end portion and said interior tube;

said unitarily molded main body further forming a second coupling nipple on said first end portion communicating with said central passageway for coupling said central passageway to the fluid delivery line;

a unitarily molded end cap mounted to said main body at said free ends of said outer shell and said interior tube, said end cap having a central passageway;

said end cap connecting said free end of said outer shell and said free end of said interior tube to close off said pressure chamber; and said central passageway of said end cap communicating with said central passageway of said interior tube to define a continuous passageway through said valve assembly, whereby flow through the delivery line and continuous passageway can be shut off by forcing pressurized fluid into the pressure chamber to collapse the interior tube.

2. A sphincter valve assembly as claimed in claim 1 and wherein said substantially flexible material comprises a rubberized plastics material.

3. A sphincter valve assembly as claimed in claim 1 and wherein said substantially flexible material comprises a latex material.

4. A sphincter valve assembly as claimed in claim 1 and wherein said substantially flexible material comprises silicone.

5. A sphincter valve assembly as claimed in claim 1 and wherein said pressure chamber is adapted to receive pressurized gas.

6. A sphincter valve assembly as claimed in claim 5 and wherein said pressurized gas comprises air.

7. A sphincter valve assembly as claimed in claim 1 and wherein said pressure chamber is adapted to receive pressurized liquid.

8. A sphincter valve comprising a body unitarily molded from a substantially flexible material, said body defining an outer shell having a free end, an interior tube disposed within said outer shell and having a free end disposed adjacent said free end of said outer shell, a pressure chamber between said interior tube and said outer shell, a first end portion, a central passageway extending through said first end portion and said interior tube, and an end cap mounted to said free ends of said outer shell and said interior tube, said end cap connecting said free ends to close off said pressure chamber and having an opening communicating with said central passageway to define a continuous passageway through said sphincter valve.

9. A sphincter valve as claimed in claim 8 and further comprising a first coupling nipple communicating with said pressure chamber for coupling said pressure camber to a source of selectively deliverable pressurized fluid.

10. A sphincter valve as claimed in claim 9 and wherein said unitarily molded main body further defines second coupling nipple and said end cap defines a third coupling nipple for splicing said continuous passageway into a fluid delivery line for flow of fluid from said fluid delivery line through said continuous passageway.

11. A sphincter valve as claimed in claim 8 and wherein said substantially flexible material comprises silicone.

12. In a sphincter valve having a first end portion, an outer shell extending from said first end portion to a free end, an interior tube disposed in said outer shell and extending from said first end portion to a free end adjacent said free end of said outer shell, a pressure chamber defined between said interior tube and said outer shell, and an end cap mounted to and connecting said free ends of said outer shell said interior tube to close off said pressure chamber, the improvement thereof wherein said outer shell, said end portion, and said interior tube are unitarily molded from a substantially flexible material.

13. The improvement of claim 12 and wherein said end cap is unitarily molded of said substantially flexible material.

14. The improvement of claim 13 and wherein said substantially flexible material comprises silicone.

15. A sphincter valve comprising a unitary main body molded from a substantially flexible material, said main body having a first end portion, an outer shell projecting from said end portion to a free end and defining the exposed outer surface of said sphincter valve, an interior tube disposed within said outer shell to define a pressure chamber between said interior tube and said outer shell, said interior tube projecting from said end portion to a free end adjacent said free end of said outer shell, and a second end portion connecting said free ends to close off said pressure chamber.

* * * * *